United States Patent [19]
Ellis

[11] Patent Number: 5,348,542
[45] Date of Patent: Sep. 20, 1994

[54] HOLDER FOR PERCUTANEOUSLY INTRODUCED TUBES

[75] Inventor: David W. Ellis, Toms River, N.J.

[73] Assignee: Joseph P. Padula, Spring Lake Heights, N.J. ; a part interest

[21] Appl. No.: 203,839

[22] Filed: Feb. 28, 1994

Related U.S. Application Data

[63] Continuation of Ser. No. 58,112, May 5, 1993, abandoned.

[51] Int. Cl.⁵ .......................... A61M 5/32; A61M 1/00
[52] U.S. Cl. ........................................ 604/173; 604/35; 604/179; 604/180; 604/284; 604/283
[58] Field of Search ................... 604/905, 27, 30, 33, 604/35, 43, 93, 173, 179, 180, 236, 237, 256, 283, 284

[56] References Cited

U.S. PATENT DOCUMENTS

| | | | |
|---|---|---|---|
| 3,572,375 | 3/1971 | Rosenberg | 604/237 |
| 3,996,923 | 12/1976 | Guerra | 604/237 |
| 4,834,719 | 5/1989 | Arenas | 604/905 |
| 5,084,026 | 1/1992 | Shapiro | 604/179 |
| 5,098,405 | 3/1992 | Peterson et al. | 604/256 |
| 5,098,410 | 3/1992 | Kerby et al. | 604/284 |
| 5,167,730 | 12/1993 | Paul | 604/179 |

FOREIGN PATENT DOCUMENTS

| 49203 | 3/1992 | World Int. Prop. O. | 504/283 |
|---|---|---|---|

*Primary Examiner*—John G. Weiss
*Attorney, Agent, or Firm*—Caesar, Rivise, Bernstein, Cohen & Pokotilow, Ltd.

[57] ABSTRACT

A holder for percutaneously introduced tubes is disclosed. The tube inserted into the body, a tube for drainage, and an entry port for medicants or irrigating fluids, are connected to the holder. The entry port has a normally closed valve which opens when medicants or irrigating fluids are introduced into the tube and which also blocks communication between the tube and the drainage tube. Similarly, the drainage tube has a normally closed valve which opens when suction is applied to the tube to allow materials or debris to be drained from the body. The holder thus protects the body at all times from the entry of air and from bacterial contamination.

6 Claims, 1 Drawing Sheet

HOLDER FOR PERCUTANEOUSLY INTRODUCED TUBES

This application is a continuation, of application Ser. No. 08/058,112, filed May 5, 1993, now abandoned.

FIELD OF THE INVENTION

This invention relates generally to devices for holding tubes introduced into the body of patients and more particularly to a holder for percutaneously introduced tubes with separate and independent means for introducing medicants or irrigating fluids into the body and for drainage or evacuation of material from the body.

Various means for anchoring percutaneously introduced tubes are known. Means for anchoring a tube for injection or drainage using adhesive materials are disclosed in Gordon et al., U.S. Pat. No. 3,135,158; Eby, U.S. Pat. No. 3,046,948; Doan, U.S. Pat. No. 3,430,300; McCormick, U.S. Pat. No. 3,683,911; and Cutruzzula et al., U.S. Pat. No. 4,059,105.

Devices which include domes which may be split over the incision into the body are disclosed in Cooke, U.S. Pat. No. 3,194,235; Weeks, U.S. Pat. No. 4,645,492; Edmunds, U.S. Pat. No. 4,767,411; and Oliver, U.S. Pat. No. 4,808,162. Similar shields are disclosed by Yamamoto et al., U.S. Pat. No. 4,915,694, which uses a pour shield with a slit cover for opening to allow the catheter to be inserted; and Kalt, U.S. Pat. No. 5,000,741, which discloses a transparent tracheostomy tube which is split and which allows viewing of the incision.

However, none of the prior art discloses a holder for percutaneously introduced tubes which securely anchors the tube inserted into the body and provides for means for infusing medicants or irrigating fluids into the body and means for evacuating materials and debris from the body which are completely independent of each other, as does the present invention.

OBJECTS OF THE INVENTION

Accordingly, it is a general object of the instant invention to provide a holder for percutaneously introduced tubes which overcomes the shortcomings of present devices.

It is a further object of the instant invention to provide a holder for percutaneously introduced tubes which securely anchors the tube through a surface of the body of the patient.

It is still a further object of the instant invention to provide a holder for percutaneously introduced tubes which provides for means for insertion of medicants or irrigating fluids into the body through the tube, as well as means for evacuating materials, fluids or debris from the body, which means are completely independent of one another.

It is still yet a further object of the instant invention to provide a holder for percutaneously introduced tubes which allows for the injection of medicants or irrigating fluids without requiring the disruption of the integrity of the drainage means.

It is another object of the instant invention to provide a holder for percutaneously introduced tubes which isolates the drainage means from the tube during the infusion of medicants or irrigating fluids.

It is still another object of the instant invention to provide a holder for percutaneously introduced tubes which isolates the port through which medicants or irrigating fluids are injected from the body tube when drainage is taking place.

It is still yet another object of the instant invention to provide a holder for percutaneously introduced tubes which is transparent and allows for visibility of the area at the junction between the body tube, the drainage tube and the entry port for infusion of medicants or irrigating fluids.

It is an additional object of the instant invention to provide a holder for percutaneously introduced tubes which provides for protection from the entry of air and from bacterial contamination during the infusion of medicants or irrigating fluids and during drainage of materials, fluids or debris from the body.

SUMMARY OF THE INVENTION

These and other objects of the invention are achieved by providing a holder for percutaneously introduced tubes which includes a connection for a tube introduced into the body, a port for the insertion of medicants or irrigating fluids into the body, and a connection for a drainage tube to remove materials, fluids or debris from the body. The port for infusion into the body includes a valve which when operated allows for communication of the port to the body tube, while isolating the input section to the drainage tube. Similarly, the drainage tube includes a valve which is normally closed and operated only during drainage. The normally closed valves insure the integrity of the holder and protect against the entry of air and/or bacterial contamination at all times including when infusion or drainage takes place.

DESCRIPTION OF THE DRAWING

Other objects and many of the intended advantages of this invention will be readily appreciated when the same becomes better understood by reference to the following detailed description when considered in connection with the accompanying drawing wherein.

DETAILED DESCRIPTION OF THE PREFERRED EMBODIMENT

Figure 1:
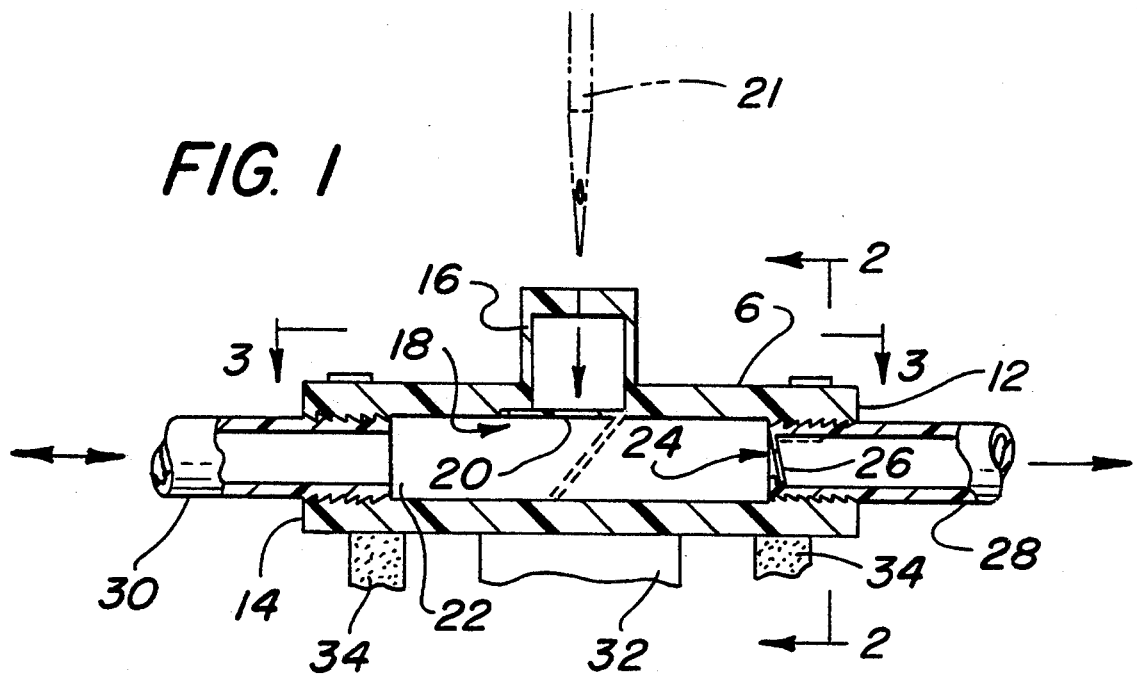
FIG. 1 is a sectional side view of the holder of the instant invention.
Figure 2:
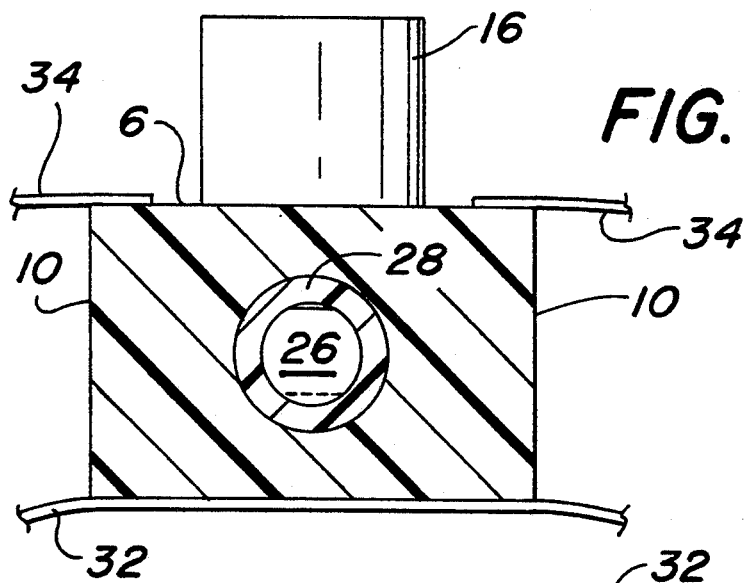
FIG. 2 is a sectional view of the holder of the instant invention taken along the line 2—2 of FIG. 1.

Referring now in greater detail to the various figures of the drawing, wherein like reference characters refer to like parts, there is shown in FIG. 1 a side sectional view of the holder 2 of the instant invention. The holder 2 is made of transparent material and comprises a hollow interior body section 4 which has a top wall 6, a bottom wall 8, two side walls 10 and end walls 12 and 14.

Protruding from the top wall 6 is cylindrically shaped hollow entry port 16. At the base of entry port 16 is a valve 18. The valve 18 comprises flap 20.

As can be seen in the figure, when an infusion needle 21, which is used for the insertion of medicants or irrigating fluids into the body, is inserted into the entry port 16, the flap 20 of the valve 18 is caused to move downward into the hollow interior body section 4 of the holder 2, as shown by the dotted lines. A percutaneously introduced tube 30 is inserted into an opening in the end wall 14 of the holder 2 and held in place by the ferruled inner surface 22 of the opening in the holder 2.

Thus, it can be seen that when the infusion needle is inserted, a normally closed valve 18, is opened, allowing for fluid communication between the infusion needle 21 and the tube 30. At the same time, the flap 20 is moved downward so as to black communication between the body tube 30 and a drainage tube 28, which has been installed in the ferruled inner surface 23 of an opening in the end wall 12 of the holder 2.

A valve 24 is installed at the input end of the drainage tube 28. This valve 24 is also normally closed. Therefore, during infusion, the fluid communication between the tube 30 and the drainage tube 28 is blocked by both the position of the flap 20 of the valve 18 and the flap 26 of the valve 24. When suction is applied to the drainage tube 28, the normally closed valve 24 operates causing flap 26 to move upward (as shown by the dashed lines) to establish fluid communication between the body tube 30 and the drainage tube 28.

Figure 3:
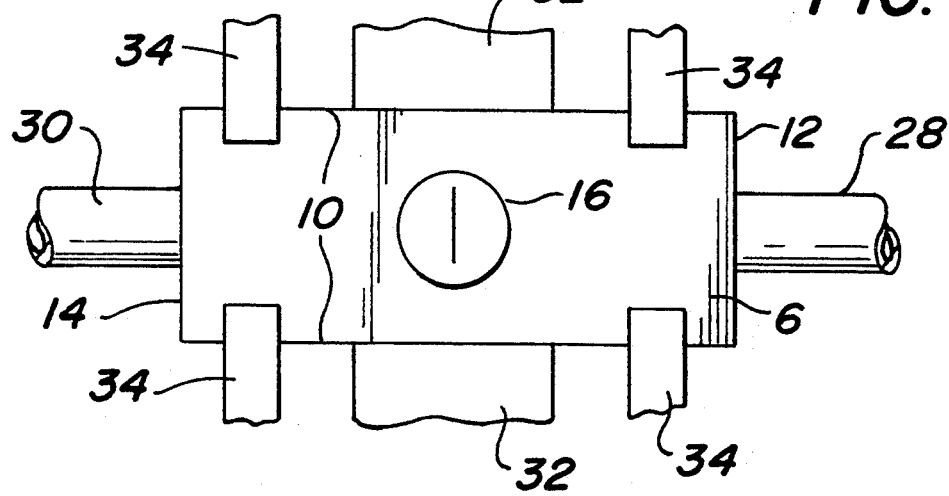
FIG. 3 is a top plan view of the holder of the instant invention taken along the line 3—3 of FIG. 1.

Referring now to FIG. 3, it is seen that a body strap 32 is attached to body section 4. The holder 2 is secured by wrapping the body strap 32 around the chest or other part of the body. The free ends of the strap 32 can be connected together either with a buckle or through the use of VELCRO. In addition, adhesive tabs 34 which are connected to the body section 4 are also used to attach the holder 2 to the body of the patient. Thus, the holder 2 is securely attached which prevents movement and helps to secure the body tube 30, which has been percutaneously introduced into the body.

A holder for percutaneously introduced tubes has been described which provides separate and independent means to introduce medicants or irrigating fluids into the body or to provide drainage of materials from the body. When medicants or irrigating fluids are infused, the integrity of the drainage means is not disrupted. Normally closed valves protect against the entry of air or bacterial communication at all times, including during infusion and during drainage.

Without further elaboration, the foregoing will so fully illustrate my invention that others may, by applying current or future knowledge, readily adapt the same for use under various conditions of service.

I claim:

1. A holder for a percutaneously introduced tube into the body of a patient, said holder comprising:

(a) connecting means for connecting said tube to said holder;
    (b) entry means for infusing at least one of a medicant and irrigating fluid into said body via said holder;
    (c) exit means for draining fluids from said body via said holder;
    (d) a first, selectively operable valve for blocking fluid communication from said entry means to said tube when in a first orientation and for providing fluid communication from said entry means to said tube when in a second orientation, said first valve being normally in said first orientation and being moved to said second orientation in response to at least one of said medicant and irrigating fluid being injected into said entry means, whereupon said at least one of said fluids is enabled to enter into said body said first valve when in said second orientation blocking fluid communication from said tube to said exit means;
    (e) a second, selectively operable valve for blocking fluid communication from said tube to said exit means when in a first blocking orientation and for providing fluid communication from said tube to said exit means when in a second drainage orientation, said second valve being normally in said first blocking orientation and movable to said second drainage orientation in response to the application of suction to said exit means, whereupon fluid from the interior of the body of said patient is enabled to drain therefrom via said exit means; and
    (f) means for securely anchoring said holder to said body.

2. The holder of claim 1 wherein said holder comprises a top wall and a bottom wall and said entry means is positioned in said top wall.

3. The holder of claim 2 wherein said holder further comprises a first and second end wall, each of which has an opening therein.

4. The holder of claim 3 wherein said opening in said first and second walls have serrated inside surfaces for gripping said tube and said drainage tube respectively.

5. The holder of claim 4 wherein said means for securely anchoring said holder to said body comprises a belt attached to said bottom wall.

6. The holder of claim 5 wherein said belt comprises a first and a second segment, and each of said segments comprise a first and second free end.

* * * * *